United States Patent [19]

Tyers et al.

[11] 4,144,889
[45] Mar. 20, 1979

[54] CARDIAC ELECTRODES FOR TEMPORARY PACING

[75] Inventors: G. Frank O. Tyers, Hershey; Howard C. Hughes, Jr., Cornwall; Kenneth Gwirtz, Hershey, all of Pa.

[73] Assignee: Research Corporation, New York, N.Y.

[21] Appl. No.: 802,034

[22] Filed: May 31, 1977

[51] Int. Cl.² ............................................. A61N 1/04
[52] U.S. Cl. ................................ 128/418; 128/419 P
[58] Field of Search ...................... 128/418, 419 P, 416

[56] References Cited

U.S. PATENT DOCUMENTS

| | | | |
|---|---|---|---|
| 3,244,174 | 4/1966 | Wesby et al. | 128/418 |
| 3,650,276 | 3/1972 | Burghele et al. | 128/418 |
| 3,724,467 | 4/1973 | Avery et al. | 128/418 |
| 4,011,875 | 3/1977 | Lehr et al. | 128/418 |

Primary Examiner—William E. Kamm
Attorney, Agent, or Firm—Cooper, Dunham, Clark, Griffin & Moran

[57] ABSTRACT

A cardiac electrode arrangement is disclosed for use in temporarily pacing the heart of a subject and comprises an electrically-conductive strip surrounded by a layer of biocompatible insulating material, which layer has openings on one face of the strip to permit exposure of a portion thereof for contact with the heart and on the other face removably accommodates and holds the stripped end of a pacer lead in contact with the strip. The electrode may be attached to the heart by clips or a single suture, and the pacer lead can be disconnected from the electrode after use by simply pulling the stripped end from under the insulating layer.

19 Claims, 6 Drawing Figures

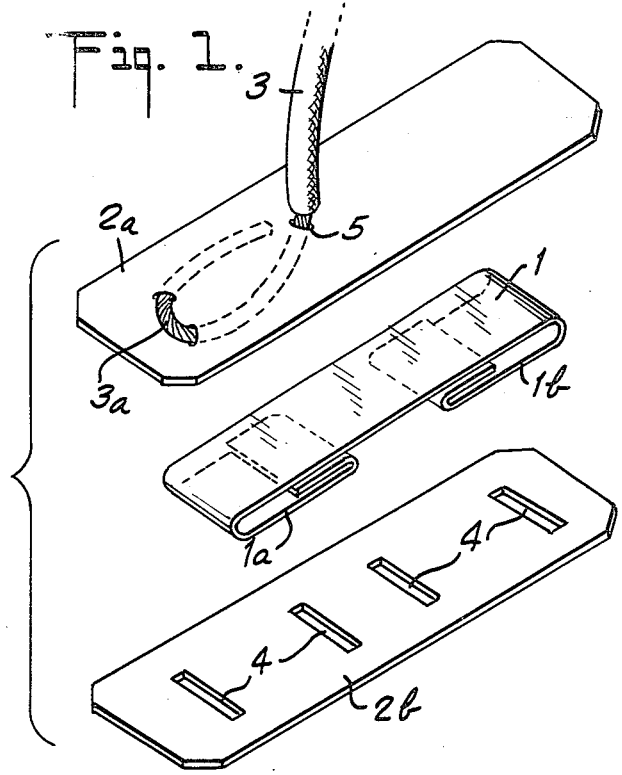
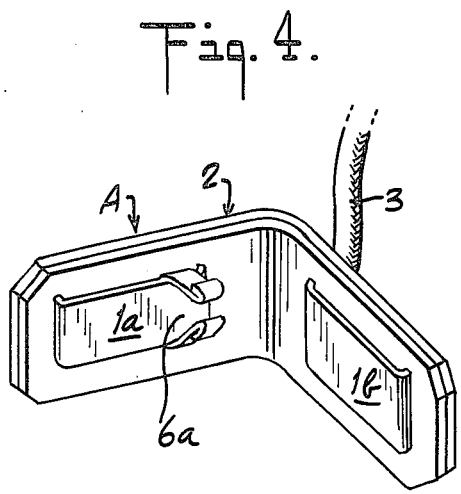
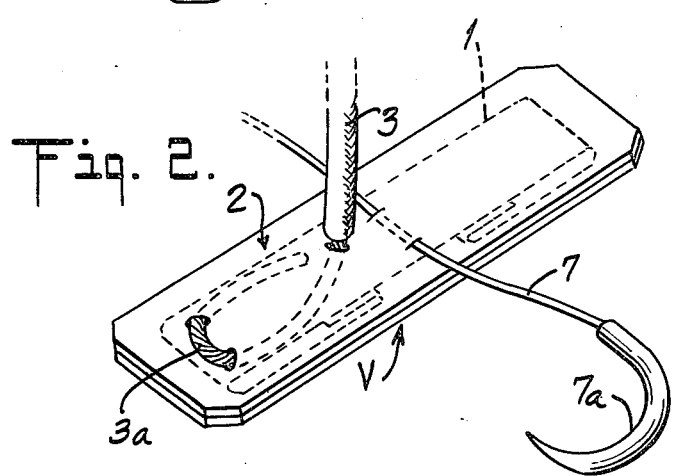
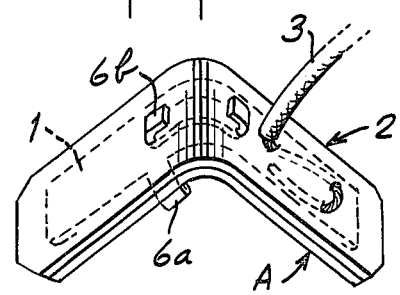
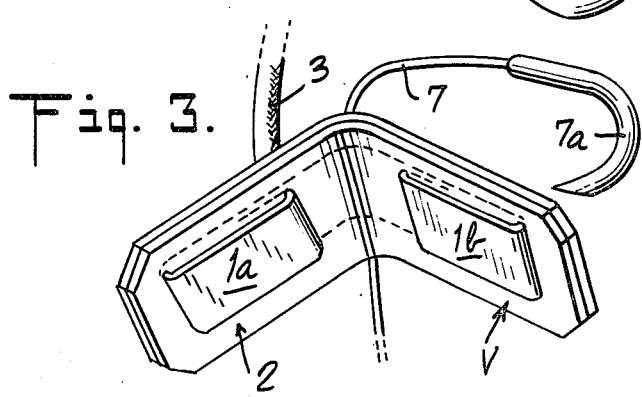
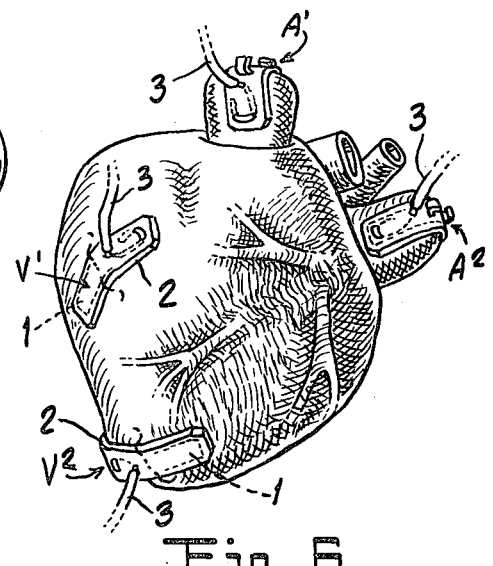

ent of the heart. Electrodes to be attached to the atria are preferably a...

CARDIAC ELECTRODES FOR TEMPORARY PACING

BACKGROUND OF THE INVENTION

The present invention relates to the cardiac pacer art and more particularly to electrodes to be attached to the heart of a subject for temporarily pacing the heart.

In many surgical and other medical situations, such as during the postoperative period, it becomes necessary to temporarily assist the heart of a patient using an external cardiac pacer. In such situations pacing electrodes must be attached to the patient's heart to perform the pacing operation. The present practice for the most part, in order to avoid the use of temporary transvenous endocardial catheters, is to simply suture the exposed ends of the insulated pacer leads to the heart for applying the electrical pulses thereto, and when the pulses are no longer needed, to pull the leads from the sutures. This prior suturing and pulling technique may result in some damage to and bleeding from the heart wall upon removal and has the further shortcomings during use of premature displacement from the myocardium, increased pacing thresholds during the postoperative period, and inadequate sensing potentials for demand pacing.

The present invention is accordingly intended to obviate these undesirable features by providing an electrode which may be easily and securely attached to the heart while permitting safe removal of the pacer lead and which adds the further advantage of a larger conductive surface area in contact with the heart for better pacing and sensing.

SUMMARY OF THE INVENTION

The present invention involves an electrode which may be clipped or singly sutured to the heart of a subject for temporarily pacing it and which electrode has an easily removable lead. The electrode basically consists of a conductive element disposed in a sleeve of insulating biocompatible material and more particularly is preferably of a laminated construction comprising a strip of biologically compatible metal, such as spring tempered stainless steel, having sheets of biocompatible material, such as silicone rubber or polyurethane, disposed on its opposite surfaces. The sheets are sealed together by silicone or other biocompatible glue to form a surrounding insulating layer or protective sleeve for the metal strip. The face of the electrode which is to contact the heart of a patient has openings in the insulating layer to permit large surface area conductive contact of the strip with the epicardium, and the stripped end of the pacer lead is held in contact with the opposite surface of the conductive strip by the other side of the insulating layer. The electrodes to be attached to the atria are preferably attached using self-fastening clips provided on the metal strip and are somewhat larger than the ventricular electrodes which are preferably attached by means of a single suture passing through the insulating layer. When no longer needed, the lead wire may be disconnected from the heart easily and safely by simply pulling the pacer lead out of the insulating sleeve leaving the electrode in undisturbed attachment on the heart.

BRIEF DESCRIPTION OF THE DRAWINGS

FIG. 1 is a perspective exploded view of an electrode in accordance with the present invention showing the basic components thereof.

FIG. 2 is a perspective view of the external side of an electrode which is adapted to act as a ventricular electrode.

FIG. 3 is a perspective view of the heart-contacting side of the electrode of FIG. 2.

FIG. 4 is a perspective view of the heart-contacting side of an electrode which is adapted to act as an atrial electrode.

FIG. 5 is a perspective view showing the opposite side of the electrode of FIG. 4.

FIG. 6 is a perspective view of two atrial and two ventricular electrodes attached to a heart.

DETAILED DESCRIPTION OF THE INVENTION

Four electrodes constructed in accordance with the present invention are shown in FIG. 6 attached to a heart. Two of the electrodes $A^1$ and $A^2$ are attached to the atrial appendages, and the other two electrodes $V^1$ and $V^2$ are attached to each of the ventricles. All are seen to essentially comprise an electrically conductive strip member 1 insulatingly surrounded by a layer of nonconductive biocompatible material 2 which forms a protective sleeve about the conductive strip. Each electrode has an insulated electrical lead 3 from a pacing generator connected thereto.

A preferred form of construction for the electrodes is shown in FIG. 1 wherein the strip member 1 is laminated between two strips or sheets or biocompatible material 2a and 2b. The strip member 1 is of a biologically compatible metal, preferably spring-tempered stainless steel, with a thickness of about 0.002 inches (0.05 mm). The biocompatible sheets 2a and 2b are preferably of silicone rubber or polyurethane and may each be about 0.02 inch (0.5 mm) thick. The metal strip 1 is embedded into the silicone rubber sheeting and the lamination is completed using an adhesive, preferably silicone glue.

The silicone rubber sheet 2b on the side of the electrode which is to contact the heart has one or more openings 4 therein to permit large surface area conductive contact between the metal strip 1 and the epicardium or surface of the heart. In the form shown the ends of the strip are passed through the appropriate openings and crimped to create large flat conductive surfaces 1a and 1b (see FIGS. 3 and 4).

The silicone rubber sheet 2a on the opposite surface of the metal strip has an opening 5 therein for accommodating the stripped end 3a of a pacer lead 3. The pacer lead 3, which is conventionally Teflon-coated stainless steel wire but which could be of other biocompatible insulation and metals, has its stripped end 3a woven between the metal strip 1 and the overlaying sheet of silicone rubber 2a in good electrical contact with the metal.

Prior to lamination the stripped lead end 3a is woven into silicone rubber sheet 2a in such manner as to permit ready removal under a pulling force, and metal strip 1 is crimped onto sheet 2b. The two sheets 2a and 2b are then brought together, and the composite structure is united and sealed using silicone glue. When dried this glue creates a sealed sleeve 2 around the wire lead which maintains its end 3a in stable electrical contact with the embedded metal strip 1. However, this construction also permits the lead 3 to be readily detached from the electrode by the application of a tension or pull on the lead which causes it to slide out from under the silicone rubber sleeve. Because the electrical connection in within the electrode, the danger of residual wire being left exposed in the chest cavity after removal is minimized. The electrode may be left on the heart after use.

It will be seen that alternate methods of constructing the electrode may be used to achieve the essential structural arrangement of a biocompatible insulating covering about the conductive electrode member, which insulating covering permits a portion of the member to contact the heart and releasably holds a pacer lead in contact with the member.

The basic electrode shown in FIG. 1 may be used as both an atrial and ventricular electrode with slight adaptation. The major differences between the atrial and ventricular electrodes are their dimensions and their mode of attachment to the heart. Firstly, as shown in FIGS. 4 and 5, an atrial electode A in accordance with the present invention may be provided by means of two clips 6a and 6b, of a suitable biocompatible metal or the like, which are attached to the metal strip 1 laminated between the two silicone rubber sheets. One clip 6a is attached to one of the conductive surfaces of strip 1 and is bent into a C-shape so as to "bite down" on the heart tissue when implanted. The other clip 6b is placed over a bend in the metal strip on the opposite side of the electrode. Spring-tempering of the metal strip facilitates the placing of a bend in it that will maintain a steady constant pressure contact of the electrode with the epicardium once implanted. Appropriate holes are formed in the silicone rubber sheet to expose the ends of clip 6b. This atrial electrode may be implanted using an applier to squeeze down on the clip 6b, thus attaching the electrode in a matter of seconds to an atrial appendage. Other self-adhering clip mechanisms are equally applicable as may be used for permanent atrial pacing electrodes.

A suitable ventricular electrode is shown in FIGS. 2 and 3. In this embodiment a single piece of suture 7 is woven through the overlying silicone rubber sheet with the needle portion 7a of the suture material still attached. During implantation the suture is passed through the myocardium only once and then tied, thereby quickly securing the electrode to the heart in the ventricular region.

Appropriate dimensions and materials which have been found suitable for the respective atrial and ventricular electrodes are set forth in the following table:

| MATERIAL AND DIMENSIONS OF ELECTRODES | | |
|---|---|---|
| A. | Atrial Electrode | |
| 1. | Silicone rubber strip dimensions | 44 × 7 × 0.5 mm |
| 2. | Stainless steel strip dimensions (total) | 64 × 3.5 × 0.05 mm |
| 3. | Atrial contact (total area) Stainless steel plates in contact with myocardium | 98 mm$^2$ 2 plates each 14 × 3.5 mm |
| 4. | Silicone rubber sheets | Dow Corning Silastic Sheeting #501-3 at 0.02" thick |
| 5. | Stainless Steel — Grade 301 | Spring tempered |
| 6. | Wound Clips | Size 7.5 mm — Clay Adams #B-2335/A (7652) |
| 7. | Glue — Silicone Type #891 | Dow Corning Medical Silastic Adhesive |
| 8. | Wire lead | "O" Flexon - Davis/Geck |
| 9. | Solder | Silver |

| —continued | | |
|---|---|---|
| MATERIAL AND DIMENSIONS OF ELECTRODES | | |
| V. | Ventricular Electrode | |
| 1. | Silicone rubber strip dimensions | 26 × 7 × 0.5 mm |
| 2. | Stainless steel strip dimensions (total) | 36 × 3.5 × 0.005 mm |
| 3. | Ventricle contact (total area) Stainless steel plates in contact with myocardium | 49.0 mm$^2$ 2 plates each 7 × 3.5 mm |
| 4. | Silicone rubber sheets | Dow Corning Silastic Sheeting #501-3 at 0.02" thick |
| 5. | Stainless steel — Grade 301 | Spring tempered |
| 6. | Glue — Silicone Type #891 | Dow Corning Medical Silastic Adhesive |
| 7. | Wire lead | "O" Flexon - Davis/Geck |
| 8. | Suture material | Variable |

The sizes and materials set forth in the table may be optimized for varying situations by, for example, reducing the overall dimensions and substituting 316-L stainless steel, titanium, or tantalum for the 301 stainless steel. It will be appreciated that since reliable demand pacing is more desirable than low energy requirements during temporary pacing with an external generator, the contact surface area used on the electrodes is made sufficiently large (50–100 mm$^2$) to ensure adequate sensing. This surface area of the metal strip in contact with the heart will, of course, be much larger than the area of contact between the strip and the stripped end of the wire lead.

We claim:

1. A cardiac electrode apparatus comprising:
   an electrically conductive electrode member;
   an insulating electrical lead having means for conductively contacting said electrode member;
   cover means of nonconductive biocompatible material for insulatingly surrounding said electrode member and holding said contacting means thereunder in conductive contact with said electrode member, said cover means comprising:
   a first insulating portion having means therein for exposing a portion of the surface of said electrode member; and
   a second insulating portion having means for releasably holding said contacting means in conductive contact with said electrode member in such manner that said contacting means is permitted to be slidably removed from under said cover means upon the imposition of a pulling force on said electrical lead; and
   means for attaching said cover means to the heart of a subject with said first insulating portion engaging the heart such that said exposed portion of the surface of said electrode member is held in conductive contact with said heart.

2. An electrode apparatus as in claim 1 wherein the area of said exposed portion of the surface of said electrode member is larger than the area of conductive contact between said contacting means and said electrode member.

3. An electrode apparatus as in claim 1 wherein said electrode member is of spring-tempered stainless steel.

4. An electrode apparatus as in claim 1 wherein said biocompatible material is silicone rubber.

5. an electrode apparatus as in claim 1 wherein said biocompatible material is polyurethane.

6. An electrode apparatus as in claim 1 wherein said attaching means comprises clip means connected to said electrode member for attaching the electrode apparatus to the heart of a subject at the atrium.

7. An electrode apparatus as in claim 1 wherein said attaching means comprises a suture means connected to said cover means for attaching the electrode apparatus to the heart of a subject at the ventricle.

8. An electrode apparatus as in claim 1 wherein said electrode member comprises a strip of metal and said first and second insulating portions comprise respective sheets of biocompatible material disposed on the opposite faces of said metal strip.

9. An electrode apparatus as in claim 8 wherein said contacting means comprises an exposed end portion of said electrical lead disposed between said metal strip and said respective sheet of biocompatible material.

10. An electrode apparatus as in claim 9 wherein said cover means further comprises biocompatible glue means for securing said sheets of biocompatible material together.

11. An electrode apparatus as in claim 10 wherein said metal is spring-tempered stainless steel and said biocompatible material and said biocompatible glue means is silicone rubber.

12. A cardiac electrode apparatus for temporarily pacing a heart comprising:
an electrically-conductive strip member;
a first layer of nonconductive biocompatible material disposed on the surface of said strip member and having means therein for exposing a portion of the surface of said strip member;
a second layer of nonconductive biocompatible material disposed on the surface of said strip member peripherally cooperating with said first layer to seal at least a portion of the edges of said strip member and having an aperture therein;
an insulated electrical lead having an uninsulated end thereon passing through said aperture and disposed under said second layer in conductive contact with said strip member and detachably held therein by such engagement with said second layer and said strip member that slidable removal is permitted by a pulling force on the electrical lead; and
means for holding said first layer in contact with the heart of a subject to produce electrical contact between said heart and said exposed portion of the surface of said strip member.

13. Apparatus as in claim 12 wherein said second layer has an additional aperture therein through which said uninsulated end passes.

14. Apparatus as in claim 12 wherein said exposed surface portion comprises an end of said strip member.

15. Apparatus as in claim 14 wherein said end is folded and crimped upon itself.

16. Apparatus as in claim 14 wherein said holding means comprises clip means on said end for engaging said heart at the atrium.

17. Apparatus as in claim 16 further comprising additional clip means connected to said strip member and passing through said second layer for applying said first-mentioned clip means to the atrium.

18. Apparatus as in claim 14 wherein said holding means comprises suture means connected to said second layer for engaging said heart at the ventricle.

19. Apparatus as in claim 14 further comprising biocompatible glue means for peripherally sealing said first and second layers together.

* * * * *